United States Patent
Bruederle et al.

(10) Patent No.: US 11,101,035 B2
(45) Date of Patent: Aug. 24, 2021

(54) SYSTEM FOR CONTROLLING A MEDICAL DEVICE

(71) Applicant: KARL STORZ SE & Co. KG, Tuttlingen (DE)

(72) Inventors: Klaus Bruederle, Tuttlingen (DE); Marco Zeller, Tuttlingen (DE); Jan Rueppell, Tuttlingen (DE); Harald Baumann, Tuttlingen (DE)

(73) Assignee: KARL STORZ SE & Co. KG, Tuttlingen (DE)

( * ) Notice: Subject to any disclaimer, the term of this patent is extended or adjusted under 35 U.S.C. 154(b) by 460 days.

(21) Appl. No.: 16/251,645

(22) Filed: Jan. 18, 2019

(65) Prior Publication Data

US 2019/0228858 A1    Jul. 25, 2019

(30) Foreign Application Priority Data

Jan. 22, 2018    (DE) .................... 10 2018 101 345.0

(51) Int. Cl.
*G16H 40/63*    (2018.01)
*G16H 40/67*    (2018.01)
(Continued)

(52) U.S. Cl.
CPC ............ *G16H 40/63* (2018.01); *A61B 34/00* (2016.02); *A61B 34/25* (2016.02); *A61B 90/00* (2016.02);
(Continued)

(58) Field of Classification Search
CPC ........ G16H 40/63; G16H 40/67; G16H 40/40; G16H 40/20; A61B 34/00; A61B 34/25;
(Continued)

(56) References Cited

U.S. PATENT DOCUMENTS 10,231,677 B2 *   3/2019   Georgiev ................ G08C 17/02
10,786,621 B2 *   9/2020   Kamen ............. A61M 5/14244
(Continued)

FOREIGN PATENT DOCUMENTS

DE      102011083957         4/2013
DE      102014208463 A1     11/2015
WO      WO 2017/025644       2/2017

OTHER PUBLICATIONS

Anonymous, Single Interactive Interface For Multiple Medical Devices, Nov. 28, 2011, IP.com PAD, 5 pages, https://ip.com/IPCOM/000212772 (Year: 2011).*

(Continued)

*Primary Examiner* — Joy Chng
(74) *Attorney, Agent, or Firm* — Jason H. Vick; Sheridan Ross, PC

(57) ABSTRACT

A system for controlling a medical device, the system comprising: a first channel and a second channel, an interface for receiving display data and control data and sending data into the first and second channels, the first channel comprising an imaging device adapted to display the display data and the control data, an image sensor adapted to detect at least an image part of the image, and an extraction device adapted to extract verification data from the image data, the second channel having a control device adapted to receive inputs from a user for and to output the control data and a control command, and a comparison device adapted to compare the test data from the extraction device and the control data from the control device.

14 Claims, 2 Drawing Sheets

(51) Int. Cl.
| | |
|---|---|
| *A61B 34/00* | (2016.01) |
| *A61B 90/00* | (2016.01) |
| *G06F 3/01* | (2006.01) |
| *G16H 40/40* | (2018.01) |
| *A61B 17/00* | (2006.01) |
| *A61B 5/1171* | (2016.01) |
| *G16H 40/20* | (2018.01) |
| *G06F 21/31* | (2013.01) |
| *G06F 21/44* | (2013.01) |

(52) U.S. Cl.
CPC .............. *G06F 3/01* (2013.01); *G16H 40/40* (2018.01); *G16H 40/67* (2018.01); *A61B 5/1171* (2016.02); *A61B 2017/00207* (2013.01); *A61B 2017/00216* (2013.01); *G06F 21/31* (2013.01); *G06F 21/44* (2013.01); *G06F 2221/2149* (2013.01); *G16H 40/20* (2018.01)

(58) Field of Classification Search
CPC .......... A61B 90/00; A61B 2017/00216; A61B 2017/00207; A61B 5/1171; G06F 3/01; G06F 21/31; G06F 21/44; G06F 2221/2149
USPC ......................................................... 705/2–3
See application file for complete search history.

(56) References Cited

U.S. PATENT DOCUMENTS

| | | | |
|---|---|---|---|
| 2013/0088452 A1* | 4/2013 | Glaser-Seidnitzer | ........................ G06F 3/0488 345/173 |
| 2013/0096575 A1* | 4/2013 | Olson | .................... A61B 34/76 606/130 |
| 2015/0223891 A1 | 8/2015 | Miller et al. | |
| 2015/0320369 A1 | 11/2015 | Jäger et al. | |
| 2019/0011905 A1* | 1/2019 | Knauder | ............ G05B 19/0426 |

OTHER PUBLICATIONS

Kasparick et al., Dynamic Remote Control Through Service Orchestration of Point-Of-Care and Surgical Devices Based on IEEE 11073 SDC, Nov. 1, 2016, 2016 IEEE Healthcare Innovation Point-Of-Care Technologies Conference (HI-POCT) (pp. 121-125), DOI: 10.1109/HIC.2016.779 (Year: 2016).*

European Search Report for corresponding European Patent Application No. 19152956.9, dated Jun. 17, 2019.

* cited by examiner

SYSTEM FOR CONTROLLING A MEDICAL DEVICE

CROSSREFERENCES TO RELATED APPLICATIONS

This application claims priority from German patent application 10 2018 101 345.0, filed on Jan. 22, 2018. The entire contents of this priority application are incorporated herein by reference.

BACKGROUND

The present disclosure is related to a system for controlling a medical device.

A surgery room contains a large number of medical devices that are used during a surgery, often using several medical devices at the same time. The medical devices usually have a control panel with which the devices can be controlled and desired settings can be made. Since the control panel is fixed and unchangeable on the corresponding medical device, only one specific medical device is controlled at a time with a specific control panel.

Due to the large number of medical devices used during a surgery, it is not possible to place all medical devices in the immediate vicinity of the user. Rather, medical devices are placed in areas where they are not in the way of doctors or assistants during a surgery. Preferably, the medical devices are located at a distance from the central surgery table in order to allow free movement. This means, however, that many medical devices can only be operated if the user moves towards the medical device.

In order to address this problem, remote controls have been introduced into the surgery room. These remote controls make it possible to operate and adjust a medical device from a distance. Although remote controls are much more compact than the medical device itself, it is difficult for a user to separate multiple remote controls during an operation and always use the correct remote control for the medical device required, especially in an emergency situation.

With regard to this problem, screens with variable display, in particular touch screens or tablet computers, have created a considerable relief. It is now possible to display data from various medical devices on the screen and, in the case of a touch-sensitive screen, to accept commands for different medical devices. The screen can display either controls for multiple devices side by side or one after the other. The various displays can be selected manually by the user or switched automatically. This allows a user to easily control multiple medical devices remotely without having to be in the immediate vicinity of these devices.

The ability to remotely control a variety of medical devices from different people using different remote controls, especially tablets, is very attractive. However, it must be ensured that at no time is an incorrect command sent to a medical device and executed there. Facilitating the operation of both medical devices must not lead to increased risks for a patient.

It is an object of the present disclosure to provide a system for controlling a medical device in which the execution of incorrect operating commands by the medical device can be prevented.

SUMMARY

According to one aspect of the disclosure there is provided a system for controlling a medical device, the system comprising
 a first channel and a second channel,
 an interface for receiving display data and control data, the interface adapted to send the display data and control data into the first channel and to send the control data into the second channel,
 the first channel comprising:
  an imaging device adapted to display the display data and the control data as an image on the imaging device,
  an image sensor adapted to detect at least an image part of the image which is displayed on the imaging device and corresponds to the control data as image data, and
  an extraction device adapted to extract verification data from the image data,
 the second channel having a control device adapted to receive inputs from a user for controlling the medical device and, in the case of an input, to output the control data and a control command, otherwise to output the control data,
 and a comparison device adapted to compare the test data from the extraction device and the control data from the control device, to determine a comparison result and to output the comparison result.

Within the scope of the disclosure, the inventors recognized that for a reliable and secure communication between a remote control, in particular a tablet computer, and a medical device, various aspects should be examined. On the one hand, a command should only be executed if it has been issued by an authorized user. The command should be derived from the context of the current process information. The sending of a command and associated information should be monitored and validated. Finally, the command flow and associated information flow should be secure and checked for integrity.

The system is a two-channel system comprising a first channel and a second channel. The system has an interface that receives display data and control data. The display data is information that is displayed on the imaging device. This includes all elements that can be displayed on the imaging device, including numeric values, text representations, graphs, and controls such as keys or buttons. The display data is configured to display on the imaging device information that is understandable to the user regarding the function of the medical device.

It should be noted that the first and second channels need not be physically separated. Rather, it is considered advantageous that the channels are not physically separated, in particular sharing one physical channel. In particular, each of the channels should be understood as a virtual signal path that transports the information packets between the components. Nevertheless, the channels are logically separated from each other, i.e. the information contained in them is isolated, especially encapsulated in messages. These messages can preferably be grouped in packets and transmitted in one frame via a common physical data transmission facility or network. Even if several components are connected to the same physical connection, the channels are separated in particular by the fact that the components either only receive such packets or only react to such packets, e.g. evaluate those that are intended for the respective component.

The control data is data that enables a distinction to be made between different data packages. Although the control data may be perceived by a user, it is not designed to be interpreted by the user, but is used for safe control, which is explained below.

The interface sends at least the received display data and control data to the first channel and sends the control data to the second channel.

In the first channel, the display data and control data are sent to the image generator, where these data are displayed as an image. The image sensor captures at least the image part of the image as image data on which the control data is displayed. An extraction device then extracts so-called test data from the image data. The test data correspond to the control data and may ideally be identical to the control data if there is no error. A deviation, on the other hand, may give an indication of an error.

A method is preferably used for extraction which reverses the conversion of the control data into information displayed on the imaging device. For example, if the control data is represented as a barcode on the imaging device, the extraction device extracts the barcode from the image data to obtain the test data. If, for example, the control data is represented as alphanumeric characters, the extraction device extracts the test data from the image data using optical character recognition (OCR).

The second channel in which the control data is sent has a control device. This control device receives input from a user who wants to control the medical device. When the controller receives the control data and the user makes an input or has made an input since the last time control data was received, the control data is output along with a control command representing the user's desired control of the medical device. If no input has been made by the user, no control command issued.

In a subsequent comparison device, the test data from the extraction device and the control data from the control device are compared and a corresponding comparison result is determined. The result of the comparison may preferably include information as to whether there is a match or no match. Depending on the design of the control data, a numerical difference between the test data and the control data may alternatively or additionally be determined as a comparison result. The comparison result is then output for further processing. If the comparison result is positive, i.e. the test data corresponds to the control data, it is assumed that the system is functioning properly. If the comparison result is negative, that is, the test data differs from the control data, an error within the system is assumed. The system may output a signal in case of a negative comparison result, e.g. an optical signal, an acoustic signal or a data signal.

The comparison or step of comparing can be performed based on a variety representations of the control data including, but not limited to, one or more of images, text, colors, shapes, letters, numbers, alphanumerical data, characters, barcodes, or symbols. For example, if the control data is represented as a first image, the second image that represents the test data is compared against the first image using known algorithms for image comparison. Also, if the control data is alphanumerical data and the second image contains data that is coded as an image, e.g. a barcode, this data may be extracted from the second image and is then compared against the alphanumerical data of the control data. In some exemplary embodiments, a full match must be found by the comparison in order to produce a positive result. In other exemplary embodiments, a threshold value is used, e.g. a fixed or variable percentage, and if the correspondence of the test data in view of the control data exceeds that threshold value, the comparison produces a positive result.

Although the system may offer many advantages over the state of the art, one special feature should be emphasized. As explained above, the display data is output together with the control data on the imaging device. If the test data corresponds to the control data in the later comparison, it is known that current control data is displayed on the imaging device. Due to the simultaneous display, this also means that current display data is displayed on the image generator. If the display on the imaging device were frozen, the user might not notice this and could send a control command based on outdated display data. Such a situation may now be detected because the frozen display means that the test data no longer matches the control data.

The system may make use of the assumption that a first delay in the first channel, i.e. from reception at the interface to reaching the comparison device, is equal to the delay in the second channel or that a delay difference between the first channel and the second channel is either known or determinable. Any difference in propagation time can then be compensated. This ensures that a deviation between the control data and the test data is not already caused by a difference in propagation time.

In an exemplary embodiment the imaging device is a screen, in particular a touch-sensitive screen, and/or the image sensor is a camera.

These elements are widely used products that have a high degree of maturity and are available on the market in many variants. In particular, it is preferable that the imaging device is a tablet computer, as a tablet computer not only has a very good screen display, but also advanced command input options and wireless communication interfaces such as WLAN or Bluetooth.

In an exemplary embodiment the imaging device is adapted to represent the control data in a predetermined area of the image and the extraction device is adapted to extract the test data from the predetermined area.

In general, it is possible to extract the control data displayed on the imaging device, provided that the area in which the control data is displayed is captured by the image sensor. For example, it is possible to capture the complete screen of the imaging device using the image sensor, even if the control data is only shown in a small part of the display. However, it is considered advantageous if the control data is displayed in a predetermined area of the image. The image sensor can then selectively evaluate the predetermined area. This makes the evaluation and acquisition of the inspection data particularly effective and reliable.

In an exemplary embodiment the imaging device is adapted to display the control data with a predetermined identifier and the extraction device is further adapted to extract the test data from an area identified by the predetermined identifier.

This embodiment enables the extraction device to quickly identify the control data shown in the image and thus extract the test data in a targeted manner. In particular, graphic elements that differ from other elements displayed on the image generator in terms of their shape and/or arrangement can be used as characteristics. For example, a 2D barcode can be used.

In an exemplary embodiment the system further comprises an image evaluation device adapted to check for a presence of a face in the image data, determine a presence result and output the presence result.

In this embodiment it is assumed that in addition to the acquisition of the image part with the control data, the image sensor also captures an area in which a face of the user making inputs with the control device should be recognizable. In this way it is possible to check whether there is a person in front of the imaging device device who is looking at the display on the imaging device. In this way, it is also possible to check whether the user is taking notice of the display on the imaging device. In addition or alternatively, when operating the control unit, it can be checked whether this was done in the presence of a user. In this way, accidental operation of the control unit can be detected.

In an exemplary embodiment wherein the image evaluating device is further adapted to identify an eye blink in a present face and to take such identification into account in determining the presence result.

This embodiment may offer additional security when checking whether a user is actually present in front of the image generator. In particular, a face is first identified in the image data, then an eye area in the face is identified and then a significant change, in particular a blink, is identified within the eye area. If a face and a blink are identified, it is highly improbable that a face has been detected by mistake or that an attempt at manipulation has been made, for example by printing a picture of a face.

In an exemplary embodiment the image evaluating device is further adapted to identify a movement of a present face and to take such identification into account in determining the presence result.

This embodiment may also increase the reliability in determining whether a user is present in front of the imaging device. A positive presence result is only displayed if both a face was identified and a movement of the identified face was detected. In another exemplary embodiment, a positive presence result is only output if a face has been identified, a blink of the eye in the face has been identified, and a movement of the face has been identified.

In an exemplary embodiment the control data has a time stamp which is taken into account in determining the comparison result such that a negative comparison result is determined if the time stamp deviates from a current time by more than a predetermined period of time.

This embodiment may allow a further verification that the system is functioning properly. It is conceivable, for example, that a time delay occurs in both the first and second channel. Although the control data and the test data may match, the time delay indicates a possible problem. If this possible problem is detected, a check or error handling can be initiated. The time stamp is preferably the current time at the time the control data is generated.

In an exemplary embodiment the control data has a sequence position that is taken into account in determining the comparison result such that a negative comparison result is determined if the sequence position does not match an expected sequence position.

In this embodiment, the control data is sent with a sequence position. This is based on the assumption that control data received in a certain sequence by the transmitting device should also arrive at the comparison device in a corresponding sequence. If the sequence position of the currently available test data and/or control data determines that it does not match the previous sequence position or positions, a negative comparison result is output.

In an exemplary embodiment the imaging device is adapted to detect a gesture performed by a user with at least one finger on the imaging device, and wherein the system further comprises an image evaluation device adapted to detect at least one of a beginning or an end of such gesture by means of the image sensor.

This embodiment is based on the assumption that the control command is executed by means of a gesture on the imaging device. In order to check whether the control command detected by the imaging device, in particular a touch-sensitive screen or tablet, was actually executed by a finger of the user. For this purpose, one or more images taken by the image sensor are evaluated by the image evaluation device. If a spatial and/or temporal agreement with regard to the detected gesture is found, there is a high degree of reliability in the sense that the detected gesture was actually performed by a user.

In an exemplary embodiment the image sensor is arranged fixedly relative to the imaging device.

This embodiment may be is relatively easy to implement. In general, it is also possible for the image sensor to be arranged in the room and from there to record the image displayed on the image generator. However, extracting the control data displayed on the image giver is particularly easy if the image pick-up is fixed to the imaging device. Depending on the desired design, both the image displayed on the imaging device and an area in front of the imaging device can be recorded to capture a face.

In an exemplary embodiment the system further comprises an enabling unit adapted to permit execution of the control command by a medical device if the comparison result is positive and to suppress the control command if the comparison result is negative.

With this embodiment, the execution of the control command can be suppressed in addition to or as an alternative to the signal function mentioned if there is an indication of a malfunction. The control command can be suppressed, for example, if the control command is not sent to the medical device or if the control command is not executed by the medical device. If the execution of a control command requires the presence of a user in front of the imaging device, the presence result can also be taken into account. Execution of the control command by the medical device is only permitted if both the comparison result and the presence result are positive. The execution is suppressed if either the comparison result or the presence result is negative. Such a check can be performed both outside the medical device, for example in a control unit, or inside the medical device itself.

In an exemplary embodiment the enabling unit is further adapted to suppress execution of the control command if the command does not correspond to the medical device of which at least one of data or controls are displayed in the image on the imaging device.

In this way it may be prevented that a control command is executed despite positive comparison result and positive presence result if the required match does not exist. For this purpose, an appropriate coding can be transmitted in the control data, for example, which is checked either before the control command is sent to a medical device or by the medical device itself. If, for example, a switch-off command reaches a first medical device, although a surface for a second medical device was displayed at the time the control command was generated, the execution of the control command is suppressed.

In an exemplary embodiment the control data is generated in the medical device and the comparison result is determined in the medical device.

This embodiment may ensure that the monitoring and verification takes place at the point where the control commands are ultimately executed and where an erroneous control command could therefore be executed. Thus it may be excluded as much as possible that an incorrect control command is still executed due subsequent causes of error.

It goes without saying that the features mentioned above and those still to be explained below can be used not only in the combination indicated, but also in other combinations or in isolation, without leaving the scope and spirit of the present disclosure.

BRIEF DESCRIPTION OF THE DRAWINGS

Exemplary embodiments of the disclosure are shown in more detail in the drawings and are explained in more detail in the following description. The figures show.

EXEMPLARY EMBODIMENTS

Figure 1:
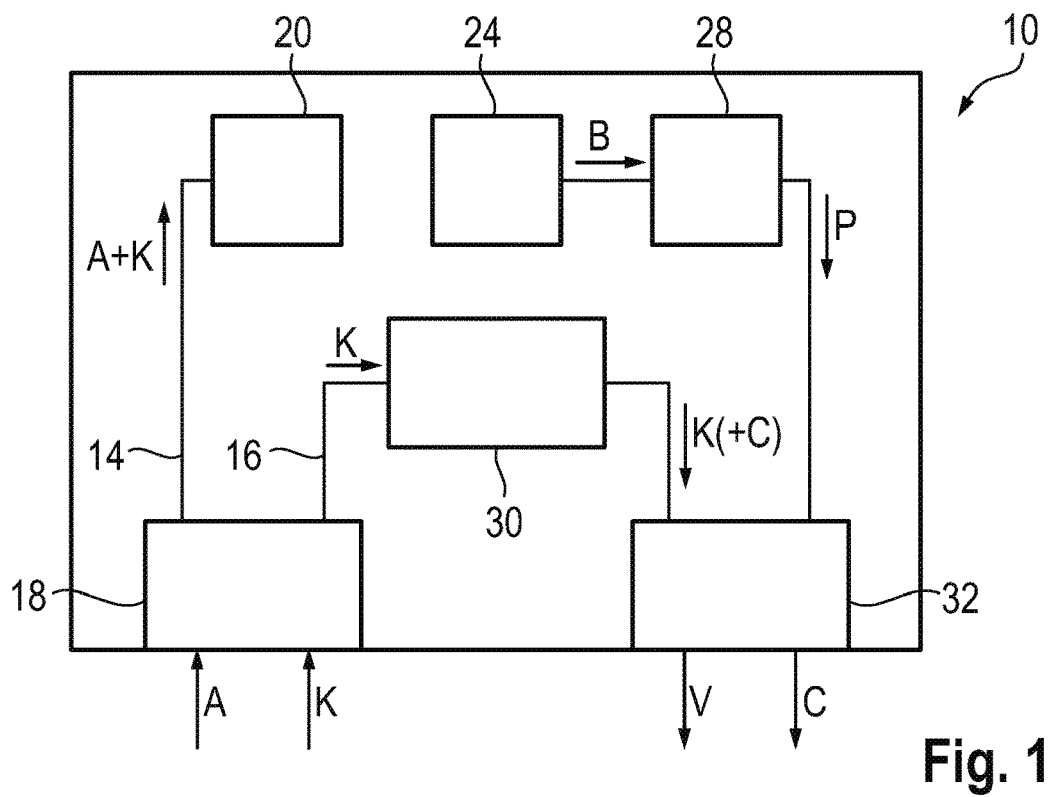
FIG. 1 is an exemplary embodiment of a system described above.
Figure 3:
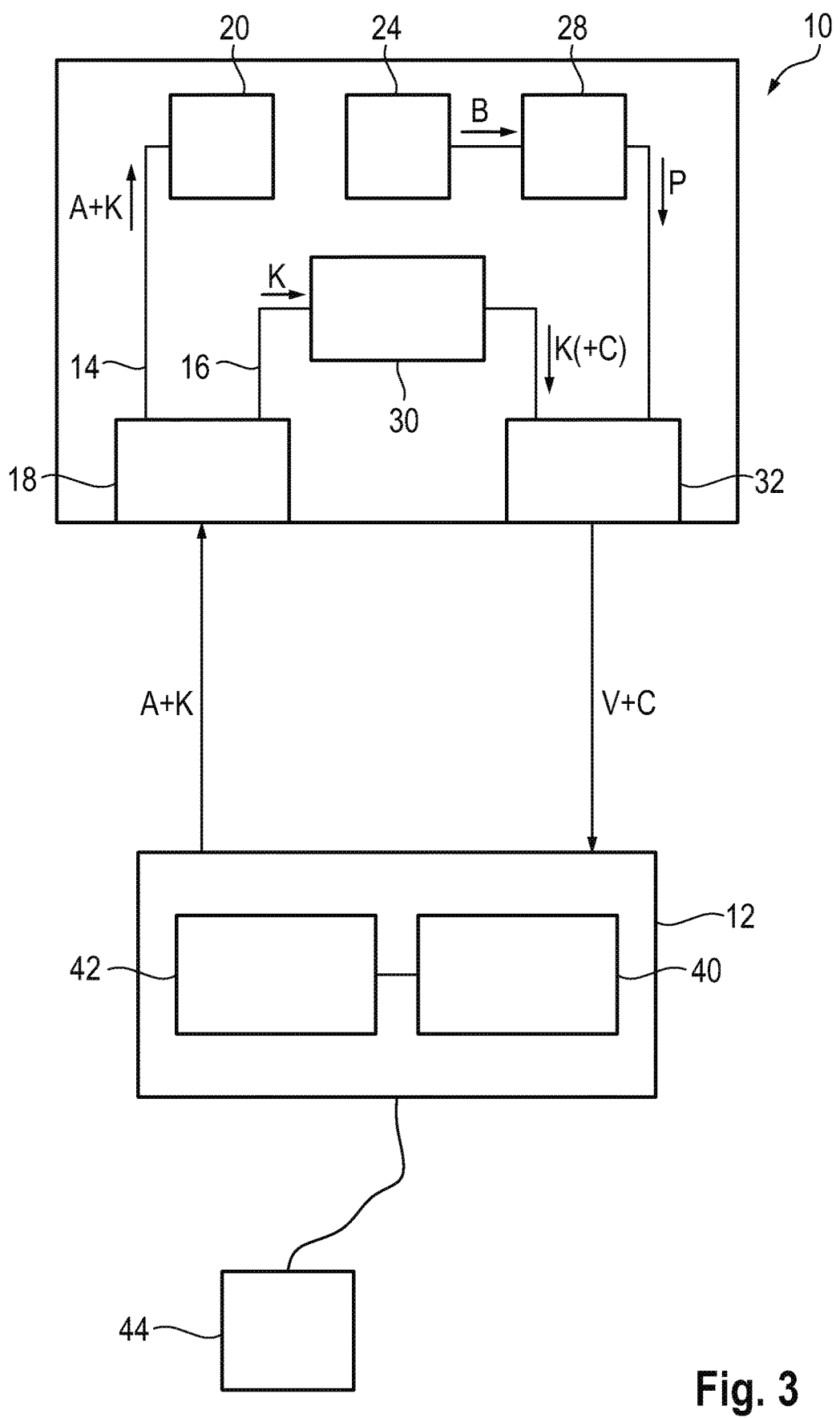
FIG. 3 the exemplary embodiment according to FIG. 2 in combination with a medical device.

FIG. 1 shows a system 10 for controlling a medical device 12 (see FIG. 3). The system 10 has a first channel 14 and a second channel 16. The system 10 also has an interface 18 for receiving display data A and control data K, where the interface 18 is designed to send the display data A and the control data K to the first channel 14 and to send the control data K to the second channel 16.

The first channel 14 has an imaging device 20, in particular a screen designed to display the display data A and the control data K as image 22 (see FIG. 2) on the imaging device 20. The first channel 14 further comprises an image sensor 24 adapted to acquire as image data B at least the image part 26 (see FIG. 2) of the image 22 represented on the imaging device 20 corresponding to the control data K. The first channel 14 further comprises extraction device 28 adapted to extract test data P from the image data B.

The second channel 16 comprises a control device 30 adapted to receive inputs from a user for controlling the medical device 12 and, in the event of an input, to output the control data K and a control command C, otherwise to output the control data K. System 10 also includes a comparison device 32 arranged to compare the test data P from extraction device 28 and the control data K from control device 30, to determine a comparison result V and to output the comparison result V. The comparison device 32 is arranged to compare the test data P from the extraction device 28 and the control data K from the control device 30, to determine a comparison result V and to output the comparison result V.

The arrows indicate that the display data A and the control data K are supplied to interface 18. It is also shown that the comparison result V and the control command C are derived from the comparison device 32. The comparison result V and the control command C can then be fed to an enabling unit 40 (see FIG. 3). However, it is also possible to integrate the enabling unit 40 in the comparison device 32 so that a control command C is only sent to the outside if the comparison result V is positive, i.e. it is sent to the medical device 12.

Figure 2:
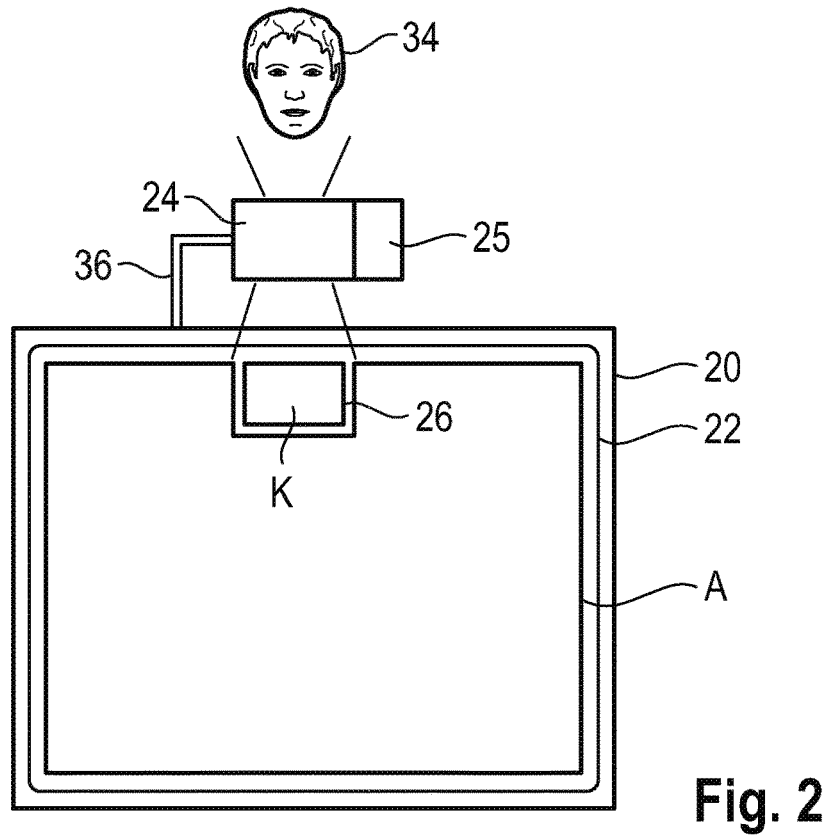
FIG. 2 is an exemplary embodiment of an imaging device in one of the systems described above.

FIG. 2 shows imaging device 20, which represents image 22. The image part 26 shows the control data K and the remaining part of the image 22 shows the display data A. An image sensor 24, in this case a camera, captures the control data K as well as a face 34 located in front of the imaging device 20. By means of a symbolic holder 36 it is indicated that the image sensor 24 is fixed to the imaging device 20.

FIG. 3 shows the system 10 according to FIG. 1 in interaction with the medical device 12. In addition to the enabling unit 40, the medical device 12 also has a device control unit 42. In the example shown here, an insufflator 44 is controlled by the medical device 12. During surgery, the medical device 12 generates display data A and control data K. The display data A is generated by the device control unit 42 and the control data K is generated by the enabling unit 40 or by the device control unit 42. The display data A and the control data K are sent to the interface 18 and pass through the first channel 14 and the second channel 16 as described above. The comparison device 32 then sends the comparison result V, here together with the control command C, back to the medical device 12. If the comparison result V is positive, the medical device 12 executes the control command C. Usually this means that a setting on the insufflator 44 is changed. If the comparison result V is negative, the release unit 40 suppresses the execution of the control command C.

In another exemplary embodiment, the test data P from the first channel 14, the control data K from the second channel 16 and the control command C are sent to the medical device 12. The comparison result V is then determined in the medical device 12. Such an embodiment has the advantage that within the medical device 12, it is also possible to check whether the control data K sent correspond to the test data P received and the control data K received. The comparison device 32 is then preferably arranged in the medical device 12. The enabling unit 40 can also check whether the control command C corresponds with the display data A. The enabling unit 40 can also check whether the control command C corresponds with the display data A.

The invention claimed is:

1. An electronic system to control a medical device comprising
    a first communications channel;
    a second communications channel,
    an interface coupled to and in communication with the first and the second communications channel, the interface receiving display data and control data, the interface sending the display data and control data into the first channel and to send the control data into the second channel,
    the first channel coupled to and in communication with:
        an imaging device displaying the display data and the control data as an image on the imaging device,
        an image sensor detecting at least an image part of the image which is displayed on the imaging device and corresponds to the control data as image data, and
        an extraction device a extracting verification data from the image data,
    the second channel coupled to and in communication with
        a control device, the control device receiving inputs from a user to control the medical device and, in the case of an input, to output the control data and a control command, otherwise to output the control data,
    and a comparison device including a processor to compare test data from the extraction device and the control data from the control device, to determine a comparison result and to output the comparison result, the comparison result indicating whether the system is functioning properly.

2. The system of claim 1, wherein the imaging device is a screen, or a touch-sensitive screen, and/or the image sensor is a camera.

3. The system of claim 1, wherein the imaging device displays the control data in a predetermined area of the image and the extraction device extracts the test data from the predetermined area.

4. The system of claim 1, wherein the imaging device displays the control data with a predetermined identifier and the extraction device extracts the test data from an area identified by the predetermined identifier.

5. The system of claim 1, further comprising an image evaluation device that checks for a presence of a face in the image data, determines a presence result and outputs the presence result.

6. The system of claim 5, wherein the image evaluating device further identifies an eye blink in a face and utilizes such identification in determining the presence result.

7. The system of claim 5, wherein the image evaluating device is further adapted to identify a movement of a present face and to take such identification into account in determining the presence result.

8. The system of claim 1, wherein the control data has a time stamp which is taken into account in determining the comparison result such that a negative comparison result is determined if the time stamp deviates from a current time by more than a predetermined period of time.

9. The system of claim 1, wherein the control data has a sequence position taken into account in determining the comparison result such that a negative comparison result is determined if the sequence position does not match an expected sequence position.

10. The system of claim 1, wherein the imaging device detects a gesture performed by a user having at least one finger on the imaging device, and wherein the system further comprises an image evaluation device that detects at least one of a beginning or an end of the such gesture detected by the image sensor.

11. The system of claim 1, wherein the image sensor is arranged fixedly relative to the imaging device.

12. The system of claim 1, further comprising an enabling unit that permits execution of the control command by a medical device if the comparison result is positive and suppresses the control command if the comparison result is negative.

13. The system of claim 12, wherein the enabling unit further suppresses execution of the control command if the command does not correspond to the medical device of which at least one of data or controls are displayed in the image on the imaging device.

14. The system of claim 1, wherein the control data is generated in the medical device and the comparison result is determined in the medical device.

* * * * *